(12) United States Patent
Neplaz et al.

(10) Patent No.: US 8,088,174 B2
(45) Date of Patent: Jan. 3, 2012

(54) METHOD FOR WASH-PROTECTING THE COLOR OF ARTIFICIALLY DYED KERATIN FIBERS

(75) Inventors: Stéphanie Neplaz, Paris (FR); Géraldine Fack, Levallois (FR); Pascale Lazzeri-Vigouroux, Puyricard (FR); Myriam Mellul, Paris (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 12/882,570

(22) Filed: Sep. 15, 2010

(65) Prior Publication Data

US 2011/0061671 A1 Mar. 17, 2011

Related U.S. Application Data

(60) Provisional application No. 61/243,265, filed on Sep. 17, 2009.

(30) Foreign Application Priority Data

Sep. 15, 2009 (FR) ...................................... 09 56336

(51) Int. Cl.
*A61Q 5/10* (2006.01)
*A61Q 5/00* (2006.01)

(52) U.S. Cl. ............. 8/405; 8/440; 8/441; 8/442; 8/497; 8/580; 132/202; 132/208; 424/70.6

(58) Field of Classification Search ............. 8/405, 440, 8/441, 442, 497, 580; 132/202, 208; 424/70.6
See application file for complete search history.

(56) References Cited

U.S. PATENT DOCUMENTS

| 3,211,618 A | 10/1965 | Kambersky et al. | |
| 2008/0229521 A1* | 9/2008 | Lalleman | ........................ 8/408 |

FOREIGN PATENT DOCUMENTS

| EP | 1 240 831 A2 | 9/2002 |
| FR | 1 299 757 | 6/1962 |
| GB | 769 082 | 2/1957 |
| GB | 2 069 335 A | 8/1981 |

OTHER PUBLICATIONS

French Search Report for FR 0956226, dated Jun. 15, 2010.

* cited by examiner

*Primary Examiner* — Eisa Elhilo
(74) *Attorney, Agent, or Firm* — Finnegan, Henderson, Farabow, Garrett & Dunner, LLP

(57) ABSTRACT

Disclosed herein is a method for wash-protecting the color of artificially dyed keratin fibers comprising applying to the artificially dyed keratin fibers at least one drying oil or at least one composition comprising, in a cosmetically acceptable medium, at least one drying oil.

18 Claims, No Drawings

METHOD FOR WASH-PROTECTING THE COLOR OF ARTIFICIALLY DYED KERATIN FIBERS

This application claims benefit of U.S. Provisional Application No. 61/243,265, filed Sep. 17, 2009. This application also claims benefit of priority under 35 U.S.C. §119 to French Patent Application No. 0956336, filed Sep. 15, 2009.

Disclosed herein is a method for wash-protecting the color of keratin fibers dyed by direct dyeing or by oxidation dyeing, such as human keratin fibers, and further such as the hair, comprising applying to the artificially dyed keratin fibers at least one drying oil.

It may be known practice to dye keratin fibers, such as human keratin fibers and further such as the hair, with dye compositions comprising oxidation dye precursors, which may be generally known as oxidation bases. These oxidation bases can be colorless or weakly colored compounds which, when combined with oxidizing agents, may give rise to colored compounds via a process of oxidative condensation. It may be also known that the shades obtained with these oxidation bases can be varied by combining them with couplers or coloration modifiers. The variety of molecules used as oxidation bases and couplers may allow a wide range of colors to be obtained.

It may be also known practice to dye keratin fibers by direct dyeing. The process that can be used in direct dyeing comprises applying to the keratin fibers direct dyes, which can be colored and coloring molecules that may have affinity for the fibers, leaving them in, and then rinsing the fibers. This direct dyeing can optionally be carried out in the presence of an oxidizing agent, reference is then made to lightening direct dyeing.

The colorations resulting therefrom can be chromatic colorations, which can be, however, temporary or semi-permanent since the nature of the interactions which bind the direct dyes to the keratin fibers and their desorption from the surface and/or the core of the fiber are responsible for their weak dyeing power and their poor wash-fastness.

The artificial color of the hair provided by a direct or oxidation dyeing treatment may gradually attenuate as a result of repeated washing and leads, over time, to fading of the coloration of the hair. The use of commercial rinse-out and leave-in care products may not sufficiently improve the fastness of the artificial color of the hair.

It may be therefore desired to develop methods for protecting the artificial color from the effect of repeated washing, e.g. for improving the color-fastness of the artificial color of the hair.

Patent EP 1312346 discloses the use of amino silicones for protecting hair color.

Provided herein is a method for wash-protecting the color of artificially dyed keratin fibers comprising applying to the artificially dyed keratin fibers at least one drying oil or a composition comprising, in a cosmetically acceptable medium, at least one drying oil.

As disclosed herein, the term "oxidizing agent" means any compound having oxidizing properties and being other than atmospheric oxygen.

The term "human keratin fibers" means the hair, body hair, including the beard or moustache, the eyelashes and the eyebrows.

The term "artificially dyed keratin fibers" means keratin fibers dyed via a direct dyeing process or via an oxidation dyeing process.

The term "washing" means at least one application to the keratin fibers of an aqueous rinse-out composition, which can include a detergent composition such as shampoo. The term also means bathing, such as in the sea or in a swimming pool.

According to at least one embodiment, the keratin fibers are dyed by oxidation dyeing, for example, in the presence of at least one oxidizing agent.

In at least one embodiment, the at least one drying oil can be introduced into the dye composition applied to the keratin fibers.

The at least one drying oil can be, for example, introduced into a composition applied before or after dyeing of the keratin fibers. According to at least one embodiment, the at least one drying oil is introduced into a composition applied after dyeing of the keratin fibers, e.g. the composition comprising the at least one drying oil is applied to the keratin fibers which have been artificially dyed beforehand.

Furthermore, the protection that can be afforded by the treatment as disclosed herein can be long-lasting.

Also provided is a method for dyeing keratin fibers, such as human keratin fibers and further such as the hair, comprising
    applying to the keratin fibers, at least one dye composition, for a time sufficient to develop the color, and
    applying to the keratin fibers a drying oil composition comprising, in a cosmetically acceptable medium, at least one drying oil.

According to at least one embodiment, the at least one dye composition is a direct dye composition or an oxidation dye composition. For example, the at least one dye composition may be an oxidation dye composition comprising at least one oxidation base.

Also provided is a method for dyeing keratin fibers comprising applying to the keratin fibers, such as human keratin fibers and further such as the hair, at least one dye composition comprising at least one direct dye and/or at least one oxidation base for a time sufficient to develop the color, wherein said at least one dye composition further comprises, in a cosmetically acceptable medium, at least one drying oil.

According to at least one embodiment, the at least one dye composition is an oxidation dye composition comprising at least one oxidation base.

The various aspects of the disclosure will now be described in detail. All the meanings and definitions of the compounds used in the present disclosure given below are valid for all the aspects of the disclosure.

The cosmetically acceptable medium for the compositions for protecting color as disclosed herein can, for example, be constituted by water, by at least one organic solvent, by oils other than drying oils or by a mixture of water and at least one cosmetically acceptable organic solvent. By way of organic solvents, mention may be made, for example, of $C_1$-$C_4$ lower alkanols, such as ethanol and isopropanol; polyols and polyol ethers, for instance 2-butoxyethanol, propylene glycol, propylene glycol monomethyl ether, diethylene glycol monoethyl ether and diethylene glycol monomethyl ether, and mixtures thereof. By way of oils other than drying oils, mention may be made, for example, of non-drying plant oils, mineral oils and liquid petroleum jelly.

Drying Oils

The term "drying oil" is intended to mean an oil which, when spread as a thin layer and then exposed to the air, becomes crosslinked and is converted into a rigid or even solid film.

For example, as disclosed herein, the term "drying oil" is intended to mean oils, and such as triglycerides, comprising double bonds, such as comprising at least two double bonds, and further such as comprising at least three double bonds. The double bonds may be conjugated or unconjugated.

The drying oils as disclosed herein may have an iodine index of greater than or equal to 90, and such as ranging from 100 to 200.

The drying oils as disclosed herein may be of natural origin.

According to at least one embodiment, the at least one drying oil can be chosen from drying plant oils, such as linseed oil, China (or Canton) wood oil also known as tung oil, oiticica oil, vernonia oil, poppyseed oil, pomegranate oil, calendula oil, and perilla oil.

The at least one drying oil as disclosed herein can be modified by physical or chemical action.

For example, it can be refined and/or partially polymerized. In this respect, mention may be made of blown oils and stand oils, maleinized oils, epoxidized oils or boiled oils.

According to at least one embodiment, the at least one drying oil is a refined linseed oil.

An oil can be refined, for example, in three successive steps.

The refined linseed oil as disclosed herein can thus result from a degumming step, in order to obtain, for example, a demucilaginated oil, followed by a decoloration step, in order to whiten it, and then by a neutralization step.

According to at least one embodiment, the at least one drying oil is a linseed oil modified according to at least one of the three abovementioned steps, for instance, which has been subjected to a degumming step, or to a decoloration step, or to a neutralization step, or to a succession of several of these steps.

According to at least one embodiment, the at least one drying oil is a drying oil which is, for example, a hot-polymerized or blown linseed drying oil.

The blowing of an oil is characterized, for example, by a partial polymerization of said oil when exposed to atmospheric oxygen. The blown oil can, for example, be obtained by blowing air through the heated oil.

The polymerization can be obtained by heating under an inert atmosphere, for example, at temperatures ranging from 250° C. to 300° C., and such as at a temperature close to 280° C. for linseed oil. The oils thus modified are called stand oils.

The at least one drying oil is, for example, can be chosen from native or refined linseed oil and linseed stand oils.

The at least one drying oil as disclosed herein may be present in the color-protecting compositions in a total amount, for example ranging from 0.05% to 100% by weight, and such as from 0.1% to 40% by weight, and further such as from 0.1% to 30% by weight, even further such as from 0.5% to 10% by weight, relative to the total weight of the composition.

The abovementioned organic solvents can be, for example, present in an amount ranging from 1% to 95% by weight, such as from 1% to 90% by weight, and further such as from 3% to 30% by weight, relative to the total weight of the composition.

The composition as disclosed herein comprising the at least one agent for protecting the color of artificially dyed keratin fibers can also comprise at least one adjuvant that can be used in hair treatment compositions, such as anionic, cationic, non-ionic, amphoteric or zwitterionic surfactants or mixtures thereof, anionic, cationic, non-ionic, amphoteric or zwitterionic polymers or blends thereof, inorganic or organic thickeners, and, for example, anionic, cationic, non-ionic and amphoteric polymeric associative thickeners, penetration agents, sequestering agents, fragrances, buffers, dispersants, conditioning agents, for instance volatile or non-volatile, modified or unmodified silicones, film-forming agents, ceramides, preservatives and opacifiers.

Conditioning Agents

The compositions as disclosed herein can, for example, comprise at least one conditioning agent, some of which can also be organic solvents.

As disclosed herein, the term "conditioning agent" means any agent of which the function is to improve the cosmetic properties of the hair, such as the softness, the disentangling, the feel, the smoothness and the static electricity.

The at least one conditioning agent may be in liquid, semi-solid or solid form such as, for example, an oil, a waxe or a gum.

According to at least one embodiment, the at least one conditioning agent may be chosen from synthetic oils such as polyolefins, non-drying plant oils, fluoro oils and perfluoro oils, natural and synthetic waxes, silicones, cationic polymers, compounds of ceramide type, cationic surfactants, fatty amines, fatty acids and esters of fatty acids other than plant oils.

The synthetic oils can be polyolefins, such as poly-α-olefins, and further such as:
  hydrogenated or nonhydrogenated polybutene type, and
    hydrogenated or nonhydrogenated polyisobutene type.
Isobutylene oligomers with a molecular weight of less than 1,000 and mixtures thereof with polyisobutylenes with a molecular weight of greater than 1,000, and such as ranging from 1,000 to 15,000, can be used.
  As examples of poly-α-olefins, mention may be made, of
    the polyisobutenes sold under the name PERMETHYL 99 A, 101 A, 102 A, 104 A (n=16) and 106 A (n=38) by the company Presperse Inc, or else the products sold under the name ARLAMOL HD (n=3) by the company ICI (n representing the degree of polymerization),
  hydrogenated or nonhydrogenated polydecene type,
  sold, for example, under the names ETHYLFLO by the company Ethyl Corp. and ARLAMOL PAO by the company ICI.

The animal or plant oils can be, for example, chosen from sunflower oil, corn oil, soya oil, avocado oil, jojoba oil, marrow oil, grapeseed oil, sesame oil, hazelnut oil, fish oils, glyceryl tricaprocaprylate, and oils of formula (I) $R_9COOR_{10}$ in which $R_9$ represents an alkyl radical comprising from 7 to 29 carbon atoms and $R_{10}$ represents a linear or branched hydrocarbon-based chain comprising from 3 to 30 carbon atoms, such as alkyl or alkenyl, for example purcellin oil.

The waxes can be natural (animal or plant) or synthetic substances that are solid at ambient temperature (20°-25° C.). They may be insoluble in water, soluble in oils and may be capable of forming a water-repellent film.

For the definition of waxes, mention may be made, for example, of P. D. Dorgan, Drug and Cosmetic Industry, December 1983, pp. 30-33.

The at least one wax is chosen, for example, from carnauba wax, candelilla wax, alfalfa wax, paraffin wax, ozokerite, plant waxes such as olive tree wax, rice wax, hydrogenated jojoba wax and the absolute waxes of flowers, such as the essential wax of blackcurrant flower sold by the company Bertin (France), animal waxes such as beeswaxes, and modified beeswaxes (cerabellina); other waxes or waxy starting materials are, for example, marine waxes such as the product sold by the company Sophim under the reference M82, and polyethylene waxes or polyolefin waxes in general.

Cationic Polymers

The at least one cationic polymer can be, for example, chosen from all those already known as improving the cosmetic properties of the hair treated with detergent compositions, for example, those described in patent publication EP- A-0 337 354 and in French patent application publications FR-A-2 270 846, 2 383 660, 2 598 611, 2 470 596 and 2 519 863.

According to at least one embodiment, the expression "cationic polymer" means any polymer comprising at least one cationic group and/or group that can be ionized into cationic groups.

For example, the cationic polymers can be chosen from those comprising primary, secondary, tertiary and/or quaternary amine groups that either may form part of the main polymer chain, or may be borne by a side substituent directly attached thereto.

The cationic polymers may have a number-average molecular mass ranging from 500 to 5,000,000, such as from 1,000 to 3,000,000.

Among the cationic polymers, mention may be made, for example, of polymers of the polyamine, polyamino amide and polyquaternary ammonium type, and cationic polymers derived from polysaccharides. Examples of the polymers of the polyamine, polyamido amide and polyquaternary ammonium type, are those described in French patent Nos. 2 505 348 or 2 542 997. Among those polymers, mention may be made of:

(1) homopolymers or copolymers derived from acrylic or methacrylic esters or amides and comprising at least one unit chosen from those of formulae (I)-(IV):

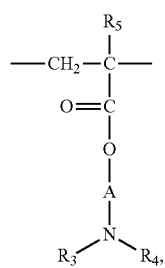
(I)

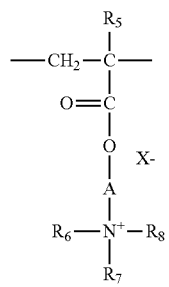
(II)

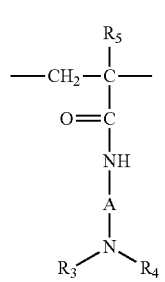
(III)

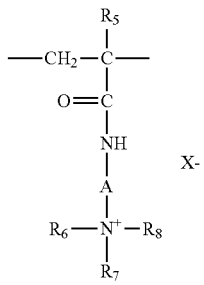
(IV)

in which:
R$_3$ and R$_4$, which may be identical or different, represent hydrogen or an alkyl group comprising from 1 to 6 carbon atoms, such as methyl or ethyl;
R$_5$, which may be identical or different, represent a hydrogen atom or a CH$_3$ radical;
A, which may be identical or different, represent a linear or branched alkyl group of 1 to 6 carbon atoms, such as 2 or 3 carbon atoms, or a hydroxyalkyl group of 1 to 4 carbon atoms;
R$_6$, R$_7$ and R$_8$, which may be identical or different, represent an alkyl group comprising from 1 to 18 carbon atoms or a benzyl radical, for example an alkyl group comprising from 1 to 6 carbon atoms;
X represents an anion derived from a mineral or organic acid, such as a methosulphate anion or a halide such as chloride or bromide.

The copolymers of family (1) can further comprise at least one unit derived from comonomers which may be chosen from acrylamides, methacrylamides, diacetone acrylamides, acrylamides and methacrylamides substituted on the nitrogen with lower (C$_1$-C$_4$) alkyls, acrylic and methacrylic acids and esters thereof, vinyllactams such as vinylpyrrolidone or vinylcaprolactam, and vinyl esters.

Thus, among these copolymers of family (1), mention may be made of:
copolymers of acrylamide and of dimethylaminoethyl methacrylate quaternized with dimethyl sulphate or with a dimethyl halide, such as the product sold under the name HERCOFLOC by the company Hercules,
the copolymers of acrylamide and of methacryloyloxyethyltrimethylammonium chloride described, for example, in patent application EP-A-080 976 and sold under the name BINA QUAT P 100 by the company Ciba Geigy,
the copolymer of acrylamide and of methacryloyloxyethyltrimethylammonium methosulphate sold under the name RETEN by the company Hercules,
quaternized or non-quaternized vinylpyrrolidone/dialkylaminoalkyl acrylate or methacrylate copolymers, such as the products sold under the name GAFQUAT by the company ISP, such as, for example, GAFQUAT 734 or GAFQUAT 755, or alternatively the products known as COPOLYMER 845, 958 and 937. These polymers are described in French patents 2 077 143 and 2 393 573,
dimethylaminoethyl methacrylate/vinylcaprolactam/vinylpyrrolidone terpolymers, such as the product sold under the name GAFFIX VC 713 by the company ISP,
vinylpyrrolidone/methacrylamidopropyldimethylamine copolymers, such as the product sold under the name STYLEZE CC 10 by ISP, and
quaternized vinylpyrrolidone/dimethylaminopropylmethacrylamide copolymers, such as the product sold under the name GAFQUAT HS 100 by the company ISP, and crosslinked polymers of methacryloyloxy($C_1$-$C_4$)alkyl ($C_1$-$C_4$)trialkylammonium salts, such as the polymers obtained by homopolymerization of dimethylaminoethyl methacrylate quaternized with methyl chloride, or by copolymerization of acrylamide with dimethylaminoethyl methacrylate quaternized with methyl chloride, the homopolymerization or copolymerization being followed by crosslinking with a compound comprising an olefinic unsaturation, such as methylenebisacrylamide. Exemplary mention may be made of an acrylamide/methacryloyloxyethyltrimethylammonium chloride crosslinked copolymer (20/80 by weight) in the form of a dispersion comprising 50% by weight of said copolymer in mineral oil. This dispersion, for example, is marketed under the name SALCARE® SC 92 by the company Ciba. Exemplary mention may also be made of a crosslinked homopolymer of methacryloyloxyethyltrimethylammonium chloride, for example as a dispersion in mineral oil or in a liquid ester. These dispersions, for example, are marketed under the names SALCARE® SC 95 and SALCARE® SC 96 by the company Ciba.

(2) Polymers constituted of piperazinyl units and of divalent alkylene or hydroxyalkylene radicals comprising straight or branched chains, optionally interrupted with oxygen, sulphur or nitrogen atoms or with aromatic or heterocyclic rings, and also the oxidation and/or quaternization products of these polymers. Such polymers are described, for example, in French patents 2 162 025 and 2 280 361.

(3) Water-soluble polyamino amides obtained, for example, by polycondensation of an acidic compound with a polyamine; these polyamino amides can be crosslinked with an epihalohydrin, a diepoxide, a dianhydride, an unsaturated dianhydride, a bis-unsaturated derivative, a bis-halohydrin, a bis-azetidinium, a bis-haloacyldiamine, a bis-alkyl halide or alternatively with an oligomer resulting from the reaction of a difunctional compound which is reactive with a bis-halohydrin, a bis-azetidinium, a bis-haloacyldiamine, a bis-alkyl halide, an epihalohydrin, a diepoxide or a bis-unsaturated derivative; the crosslinking agent can be used in an amount ranging from 0.025 to 0.35 mol per amine group of the polyamino amide; these polyamino amides can be alkylated or, if they comprise at least one tertiary amine function, they can be quaternized. Such polymers are described, for example, in French patents 2 252 840 and 2 368 508.

(4) The polyamino amide derivatives resulting from the condensation of polyalkylene polyamines with polycarboxylic acids followed by alkylation with difunctional agents. Mention may be made, for example, of adipic acid/dialkylaminohydroxyalkyldialkylenetriamine polymers in which the alkyl radical comprises from 1 to 4 carbon atoms, such as methyl, ethyl or propyl. Such polymers are described, for example, in French patent 1 583 363.

Among these derivatives, mention may be made, for example, of the adipic acid/dimethylaminohydroxypropyl/diethylenetriamine polymers sold under the name CARTARETINE F, F4 or F8 by the company Sandoz.

(5) The polymers obtained by reaction of a polyalkylene polyamine comprising two primary amine groups and at least one secondary amine group with a dicarboxylic acid chosen from diglycolic acid and saturated aliphatic dicarboxylic acids comprising from 3 to 8 carbon atoms. The molar ratio between the polyalkylene polyamine and the dicarboxylic acid ranges from 0.8:1 to 1.4:1; the polyamino amide resulting therefrom being reacted with epichlorohydrin in a molar ratio of epichlorohydrin relative to the secondary amine group of the polyamino amide ranging from 0.5:1 to 1.8:1. Such polymers are described, for example, in U.S. Pat. Nos. 3,227,615 and 2,961,347.

Polymers of this type are sold, for example, under the name HERCOSETT 57 by the company Hercules Inc. or alternatively under the name PD 170 or Delsette 101 by the company Hercules in the case of the adipic acid/epoxypropyl/diethylenetriamine copolymer.

(6) Cyclopolymers of alkyldiallylamine or of dialkyldiallylammonium, such as homopolymers or copolymers comprising, as main constituent of the chain, units corresponding to formula (V) or (VI):

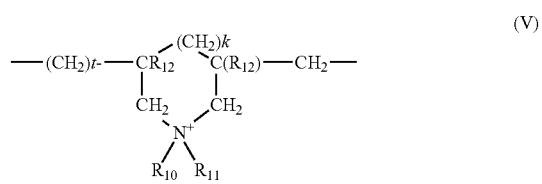

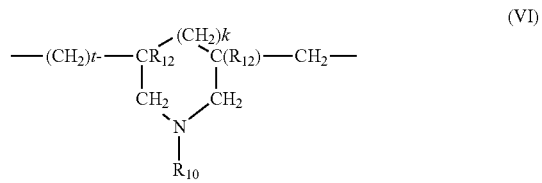

in which k and t are equal to 0 or 1, the sum k+t being equal to 1; $R_{12}$ represents a hydrogen atom or a methyl radical; $R_{10}$ and $R_{11}$, independently of each other, represent an alkyl group comprising from 1 to 6 carbon atoms, a hydroxyalkyl group in which the alkyl group, for example, comprises 1 to 5 carbon atoms, a lower ($C_1$-$C_4$) amidoalkyl group, or $R_{10}$ and $R_{11}$ can represent, together with the nitrogen atom to which they are attached, heterocyclic groups such as piperidyl or morpholinyl; $Y^-$ is an anion such as bromide, chloride, acetate, borate, citrate, tartrate, bisulphate, bisulphite, sulphate or phosphate. These polymers are described, for example, in French patent 2 080 759 and in its Certificate of Addition 2 190 406.

According to at least one embodiment, $R_{10}$ and $R_{11}$, independently of each other, represent an alkyl group comprising from 1 to 4 carbon atoms.

Among the polymers defined above, mention may be made, for example, of the dimethyldiallylammonium chloride homopolymer sold under the name MERQUAT 100 by the company Nalco (and its homologues of low weight-average molecular mass) and the copolymers of diallyldimethylammonium chloride and of acrylamide, sold under the name MERQUAT 550.

(7) The quaternary diammonium polymer comprising repeating units corresponding to the formula:

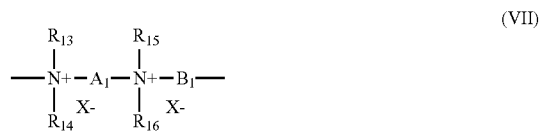

in which $R_{13}$, $R_{14}$, $R_{15}$ and $R_{16}$, which may be identical or different, represent aliphatic, alicyclic or arylaliphatic radicals comprising from 1 to 20 carbon atoms or lower hydroxyalkylaliphatic radicals, or alternatively $R_{13}$, $R_{14}$, $R_{15}$ and $R_{16}$, together or separately, constitute, with the nitrogen atoms to which they are attached, heterocycles optionally comprising a second heteroatom other than nitrogen, or alternatively $R_{13}$, $R_{14}$, $R_{15}$ and $R_{16}$, which may be identical or different, represent a linear or branched $C_1$-$C_6$ alkyl radical substituted with a nitrile, ester, acyl or amide group or a group —CO—O—$R_{17}$-D or —CO—NH—$R_{17}$-D where $R_{17}$ is an alkylene and D is a quaternary ammonium group;

$A_1$ and $B_1$ represent polymethylene groups comprising from 2 to 20 carbon atoms which may be linear or branched, saturated or unsaturated, and which may comprise, linked to or intercalated in the main chain, at least one aromatic ring, or at least one group chosen from oxygen and sulphur, or sulphoxide, sulphone, disulphide, amino, alkylamino, hydroxyl, quaternary ammonium, ureido, amide or ester groups, and $X^-$ represents an anion derived from a mineral or organic acid;

$A_1$, $R_{13}$ and $R_{15}$ can form, with the two nitrogen atoms to which they are attached, a piperazine ring; in addition, if $A_1$ represents a linear or branched, saturated or unsaturated alkylene or hydroxyalkylene radical, $B_1$ can also represent a $(CH_2)_n$—CO-D-OC—$(CH_2)_p$— group, n and p being integers ranging from 2 to 20, in which D represents:

a) a glycol residue of formula: —O—Z—O—, where Z represents a linear or branched hydrocarbon-based radical or a group corresponding to one of the following formulae:

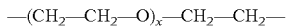

—$(CH_2$—$CH_2$—$O)_x$—$CH_2$—$CH_2$—

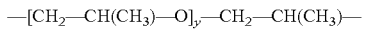

—$[CH_2$—$CH(CH_3)$—$O]_y$—$CH_2$—$CH(CH_3)$— where x and y represent an integer from 1 to 4, representing a defined and unique degree of polymerization or any number from 1 to 4 representing an average degree of polymerization;

b) a bis-secondary diamine residue such as a piperazine derivative;

c) a bis-primary diamine residue of formula: —NH—Y—NH—, where Y represents a linear or branched hydrocarbon-based radical, or alternatively the divalent radical

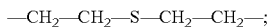

—$CH_2$—$CH_2$—S—$CH_2$—$CH_2$—;

d) a urea group of formula: —NH—CO—NH—.

According to at least one embodiment, $X^-$ is an anion such as chloride or bromide.

These polymers may have a number-average molecular mass ranging from 1,000 to 100,000.

Polymers of this type are described, for example, in French patents 2 320 330, 2 270 846, 2 316 271, 2 336 434 and 2 413 907 and U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945, and 4,027,020.

Mention may, for example, be made of polymers which comprise repeating units corresponding to the formula:

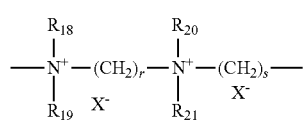

(VIII)

in which $R_{18}$, $R_{19}$, $R_{20}$ and $R_{21}$, which may be identical or different, represent an alkyl or hydroxyalkyl radical comprising from 1 to 4 carbon atoms, r and s are integers ranging from 2 to 20, and $X^-$ is an anion derived from a mineral or organic acid.

According to at least one embodiment, the compound is such that $R_{18}$, $R_{19}$, $R_{20}$ and $R_{21}$ represent a methyl radical and r=3, s=6 and X=Cl, which is referred to as hexadimethrine chloride according to the INCI nomenclature (CTFA).

(8) Polyquaternary ammonium polymers constituted of units of formula (IX):

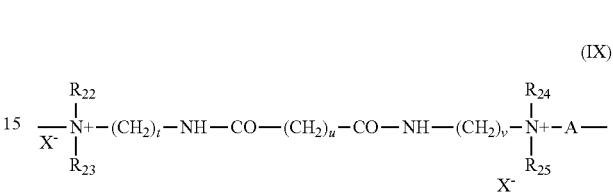

in which:

$R_{22}$, $R_{23}$, $R_{24}$ and $R_{25}$, which may be identical or different, represent a hydrogen atom or a methyl, ethyl, propyl, β-hydroxyethyl, β-hydroxypropyl or —$CH_2CH_2$ $(OCH_2CH_2)_p$OH radical, where p is equal to 0 or to an integer ranging from 1 to 6, with the proviso that $R_{22}$, $R_{23}$, $R_{24}$ and $R_{25}$ do not simultaneously represent a hydrogen atom;

t and u, which may be identical or different, are integers ranging from 1 to 6;

v is equal to an integer ranging from 0 to 34;

$X^-$ represents an anion such as a halide;

A represents a radical of a dihalide or, for example, represents —$CH_2$—$CH_2$—O—$CH_2$—$CH_2$—.

Those compounds are, for example, described in patent application EP-A-122 324.

Among these products, mention may, for example, be made of the products MIRAPOL® A 15, MIRAPOL® AD1, MIRAPOL® AZ1 and MIRAPOL® 175 sold by the company Miranol.

(9) Quaternary polymers of vinylpyrrolidone and of vinylimidazole, such as, for example, the products sold under the names LUVIQUAT® FC 905, FC 550 and FC 370 by the company BASF.

(10) Cationic polysaccharides, such as celluloses and cationic galactomannan gums.

Among the cationic polysaccharides, mention may, for example, be made of cellulose ether derivatives comprising quaternary ammonium groups, cationic cellulose copolymers or cellulose derivatives grafted with a water-soluble quaternary ammonium monomer and cationic galactomannan gums.

The cellulose ether derivatives comprising quaternary ammonium groups are, for example, described in French Patent 1 492 597. Those polymers are also defined in the CTFA dictionary as hydroxyethylcellulose quaternary ammoniums that have reacted with an epoxide substituted with a trimethylammonium group.

The cationic cellulose copolymers or the cellulose derivatives grafted with a water-soluble quaternary ammonium monomer are described, for example, in U.S. Pat. No. 4,131, 576, such as hydroxyalkylcelluloses, for instance hydroxymethyl-, hydroxyethyl- or hydroxypropylcelluloses grafted, for example, with a methacryloylethyltrimethylammonium, methacrylamidopropyltrimethylammonium or dimethyldiallylammonium salt.

The cationic galactomannan gums are described, for example in U.S. Pat. Nos. 3,589,578 and 4,031,307, such as guar gums comprising trialkylammonium cationic groups. Use is made, for example, of guar gums modified with a salt (e.g. chloride) of 2,3-epoxypropyltrimethylammonium.

Other cationic polymers as disclosed herein can be cationic proteins or cationic protein hydrolysates, polyalkyleneimines, such as polyethyleneimines, polymers comprising vinylpyridine or vinylpyridinium units, condensates of polyamines and of epichlorohydrin, quaternary polyureylenes and chitin derivatives.

The cationic proteins or protein hydrolysates are, for example, chemically modified polypeptides bearing quaternary ammonium groups at the end of the chain or grafted onto said chain. Their molecular mass may range, for example, from 1,500 to 10,000, such as from 2,000 to 5,000. Among those compounds, mention may, for example, be made of:

- hydrolysates of collagen bearing triethylammonium groups, such as the products sold under the name QUAT-PRO E by the company Maybrook and called, in the CTFA dictionary, Triethonium Hydrolyzed Collagen Ethosulphate;
- hydrolysates of collagen bearing trimethylammonium and trimethylstearylammonium chloride groups, such as the products sold under the name QUAT-PRO S by the company Maybrook and called, in the CTFA dictionary, Steartrimonium Hydrolyzed Collagen;
- hydrolysates of animal proteins bearing trimethylbenzylammonium groups, such as the products sold under the name CROTEIN BTA by the company Croda and called, in the CTFA dictionary, Benzyltrimonium hydrolyzed animal protein;
- hydrolysates of proteins bearing, on the polypeptide chain, quaternary ammonium groups comprising at least one alkyl radical comprising from 1 to 18 carbon atoms.

Among these protein hydrolysates, mention may be made, inter alia, of:

- CROQUAT L, the quaternary ammonium groups of which comprise a $C_{12}$ alkyl group;
- CROQUAT M, the quaternary ammonium groups of which comprise $C_{10}$-$C_{18}$ alkyl groups;
- CROQUAT S, the quaternary ammonium groups of which comprise a $C_{18}$ alkyl group;
- CROTEIN Q, the quaternary ammonium groups of which comprise at least one alkyl group comprising from 1 to 18 carbon atoms.

Those various products are sold, for example, by the company Croda.

Other quaternized proteins or hydrolysates are, for example, those corresponding to formula (X):

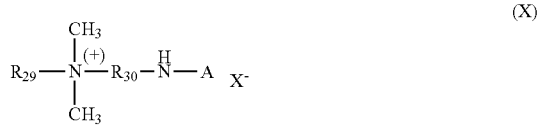

in which $X^-$ is an anion of an organic or mineral acid, A represents a protein residue derived from collagen protein hydrolysates, $R_{29}$ represents a lipophilic group comprising up to 30 carbon atoms, $R_{30}$ represents an alkylene group comprising from 1 to 6 carbon atoms. Mention may, for example, be made of the products sold by the company Inolex, under the name LEXEIN QX 3000, called, in the CTFA dictionary, Cocotrimonium Collagent Hydrolysate.

Mention may also be made of quaternized plant proteins, such as wheat, corn or soya proteins: as quaternized wheat proteins, mention may be made of those sold by the company Croda under the names HYDROTRITICUM WQ or QM, called, in the CTFA dictionary, Cocodimonium Hydrolysed wheat protein; HYDROTRITICUM QL, called, in the CTFA dictionary, Laurdimonium hydrolysed wheat protein; or else HYDROTRITICUM QS, called, in the CTFA dictionary, Steardimonium hydrolysed wheat protein.

According to at least one embodiment, the cationic polymers can be cationic cyclopolymers, such as the dimethyldiallylammonium chloride homopolymers or copolymers sold under the names MERQUAT 100, MERQUAT 550 and MERQUAT S by the company Nalco, and quaternary vinylpyrrolidone and vinylimidazole polymers, cationic polysaccharides and mixtures thereof.

Silicones

The silicones that may be used in accordance with the disclosure are, for example, polyorganosiloxanes that are insoluble in the composition and that may be in the form of oils, waxes, resins or gums.

The organopolysiloxanes are defined in greater detail, for example, in Walter Noll's "Chemistry and Technology of Silicones" (1968) Academic Press. They can be volatile or non-volatile.

When they are volatile, the silicones are, for example, chosen from those having a boiling point ranging from 60° C. and 260° C., and such as from:

(i) cyclic silicones comprising from 3 to 7 and such as from 4 to 5 silicon atoms. Those are, for example, octamethylcyclotetrasiloxane sold under the name VOLATILE SILICONE 7207 by Union Carbide or SILBIONE 70045 V 2 by Rhodia Chimie, decamethylcyclopentasiloxane sold under the name VOLATILE SILICONE 7158 by Union Carbide, and SILBIONE 70045 V 5 by Rhodia Chimie, and mixtures thereof.

Mention may also be made of cyclocopolymers of the dimethylsiloxanes/methylalkylsiloxane type, such as Volatile Silicone FZ 3109 sold by the company Union Carbide, having the chemical structure:

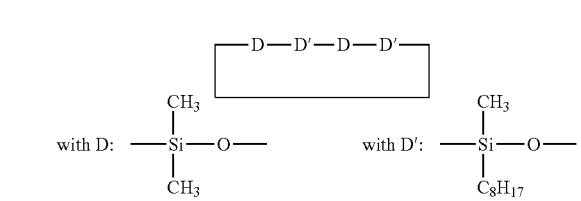

Mention may also be made of mixtures of cyclic silicones with organosilicon compounds, such as the mixture of octamethylcyclotetrasiloxane and tetratrimethylsilylpentaerythritol (50/50) and the mixture of octamethylcyclotetrasiloxane and oxy-1,1'-bis(2,2,2',2',3,3'-hexatrimethylsilyloxy)neopentane;

(ii) linear volatile silicones comprising 2 to 9 silicon atoms and having a viscosity of less than or equal to $5 \times 10^{-6}$ m$^2$/s at 25° C. An example is decamethyltetrasiloxane sold, for example, under the name SH 200 by the company Toray Silicone. Silicones belonging to this category are also described, for example, in the article published in Cosmetics and Toiletries, Vol. 91, Jan. 76, pp. 27-32, Todd & Byers "Volatile Silicone Fluids for Cosmetics."

According to at least one embodiment, the silicones are non-volatile silicones, and for example, polyalkylsiloxanes, polyarylsiloxanes, polyalkylarylsiloxanes, silicone gums and resins, polyorganosiloxanes modified with organofunctional groups, and mixtures thereof.

Those silicones are, for example, chosen from polyalkylsiloxanes, among which mention may be made, for example, of polydimethylsiloxanes comprising trimethylsilyl end groups having a viscosity of from $5\times10^{-6}$ to 2.5 m²/s at 25° C. and such as $1\times10^{-6}$ to 1 m²/s. The viscosity of the silicones is measured, for example, at 25° C. according to ASTM standard 445 Appendix C.

Among these polyalkylsiloxanes, mention may be made, in a non-limiting manner, of the following commercial products:
- the SILBIONE oils of the 47 and 70 047 series or the MIRASIL oils sold by Rhodia Chimie, such as, for example, the oil 70 047 V 500 000;
- the oils of the MIRASIL series sold by the company Rhodia Chimie;
- the oils of the 200 series from the company Dow Corning, such as, DC200 with a viscosity of 60,000 cSt;
- the VISCASIL oils from General Electric and certain oils of the SF series (SF 96, SF 18) from General Electric.

Mention may also be made of polydimethylsiloxanes comprising dimethylsilanol end groups (Dimethiconol according to the CTFA name) such as the oils of the 48 series from the company Rhodia Chimie.

In this category of polyalkylsiloxanes, mention may also be made of the products sold under the names ABIL WAX 9800 and 9801 by the company Goldschmidt, which are poly($C_1$-$C_{20}$)alkylsiloxanes.

The polyalkylarylsiloxanes can be chosen from linear and branched polydimethylmethylphenylsiloxanes and polydimethyldiphenylsiloxanes with a viscosity of from $1\times10^{-5}$ to $5\times10^{-2}$ m²/s at 25° C.

Among these polyalkylarylsiloxanes, mention may be made, by way of example, of the products sold under the following names:
- the SILBIONE oils of the 70 641 series from Rhodia Chimie;
- the oils of the RHODORSIL 70 633 and 763 series from Rhodia Chimie;
- the oil DOW CORNING 556 Cosmetic Grade Fluid from Dow Corning;
- the silicones of the PK series from Bayer, such as the product PK20;
- the silicones of the PN and PH series from Bayer, such as the products PN1000 and PH1000;
- certain oils of the SF series from General Electric, such as SF 1023, SF 1154, SF 1250 and SF 1265.

The silicone gums as disclosed herein can be, for example, polydiorganosiloxanes with high number-average molecular masses ranging from 200,000 to 1,000,000, used alone or as a mixture in a solvent. This solvent can be chosen from volatile silicones, polydimethylsiloxane (PDMS) oils, polyphenylmethylsiloxane (PPMS) oils, isoparaffins, polyisobutylenes, methylene chloride, pentane, dodecane and tridecanes, and mixtures thereof.

Mention may be made, for example, of the following products:
- polydimethylsiloxane gums,
- polydimethylsiloxane/methylvinylsiloxane gums,
- polydimethylsiloxane/diphenylsiloxane gums,
- polydimethylsiloxane/phenylmethylsiloxane gums,
- polydimethylsiloxane/diphenylsiloxane/methylvinylsiloxane gums.

Products that can be used in accordance with the disclosure are mixtures such as:
- mixtures formed from a polydimethylsiloxane hydroxylated at the chain end (referred to as dimethiconol according to the nomenclature in the CTFA dictionary) and from a cyclic polydimethylsiloxane (referred to as cyclomethicone according to the nomenclature in the CTFA dictionary), such as the product Q2 1401 sold by the company Dow Corning;
- mixtures formed from a polydimethylsiloxane gum with a cyclic silicone, such as the product SF 1214 SILICONE FLUID from the company General Electric; this product is an SF 30 gum corresponding to a dimethicone, having a number-average molecular weight of 500,000, dissolved in the oil SF 1202 Silicone Fluid corresponding to decamethylcyclopentasiloxane;
- mixtures of two PDMSs with different viscosities, such as of a PDMS gum and a PDMS oil, such as the product SF 1236 from the company General Electric. The product SF 1236 is a mixture of an SE 30 gum defined above, having a viscosity of 20 m²/s, and an SF 96 oil, with a viscosity of $5\times10^{-6}$ m²/s. This product, for example, contains 15% SE 30 gum and 85% SF 96 oil.

The organopolysiloxane resins that can be used in accordance with the disclosure are crosslinked siloxane systems comprising the following units:
$R_2SiO_{2/2}$, $R_3SiO_{1/2}$, $RSiO_{3/2}$ and $SiO_{4/2}$ in which R represents a hydrocarbon-based group comprising 1 to 16 carbon atoms or a phenyl group. Among those products, mention may be made of the ones in which R represents a $C_1$-$C_4$ lower alkyl radical, such as methyl, or a phenyl radical.

Among those resins, mention may be made of the product sold under the name DOW CORNING 593 or those sold under the names SILICONE FLUID SS 4230 and SS 4267 by the company General Electric, which are silicones of dimethyl/trimethyl siloxane structure.

Mention may also be made of the trimethyl siloxysilicate type resins sold, for example, under the names X22-4914, X21-5034 and X21-5037 by the company Shin-Etsu.

The organomodified silicones that can be used in accordance with the disclosure can be silicones as defined above and comprising in their structure at least one organofunctional group attached via a hydrocarbon-based radical.

Among the organomodified silicones, mention may be made of polyorganosiloxanes comprising:
- polyethyleneoxy and/or polypropyleneoxy groups optionally comprising $C_6$-$C_{24}$ alkyl groups, such as the products known as DIMETHICONE COPOLYOL sold by the company Dow Corning under the name DC 1248 or the oils SILWET L 722, L 7500, L 77 and L 711 by the company Union Carbide, and the ($C_{12}$)alkylmethicone copolyol sold by the company Dow Corning under the name Q2 5200;
- substituted or unsubstituted amine groups, such as the products sold under the name GP 4 SILICONE FLUID and GP 7100 by the company Genesee, or the products sold under the names Q2 8220 and DOW CORNING 929 or 939 by the company Dow Corning. The substituted amine groups are, for example, $C_1$-$C_4$ aminoalkyl groups;
- thiol groups such as the products sold under the names GP 72 A and GP 71 from Genesee;
- alkoxylated groups such as the product sold under the name SILICONE COPOLYMER F-755 by SWS Silicones and ABIL WAX 2428, 2434 and 2440 by the company Goldschmidt;
- hydroxylated groups such as the polyorganosiloxanes comprising a hydroxyalkyl function, described, for example, in French patent application FR-A-85/16334, corresponding to formula (XI):

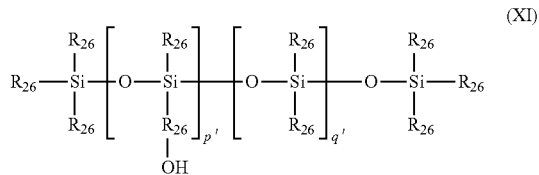

(XI)

in which the radicals $R_{26}$, which may be identical or different, are chosen from methyl and phenyl radicals; at least 60 mol % of the radicals $R_{26}$ representing methyl; the radical $R'_{26}$ is a $C_2$-$C_{18}$ divalent hydrocarbon-based alkylene chain unit; p' is an integer ranging from 1 to 30; q' is an integer ranging from 1 to 150;

acyloxyalkyl groups such as, for example, the polyorganosiloxanes described in U.S. Pat. No. 4,957,732 and corresponding to formula (XII):

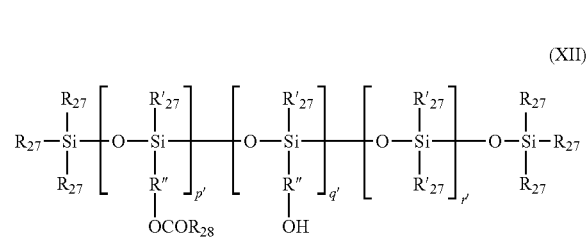

(XII)

in which:

$R_{27}$, which may be identical or different, represent a methyl, phenyl, —$OCOR_{28}$ or hydroxyl group, one of the radicals $R_{27}$ per silicon atom possibly being OH;

$R'_{27}$, which may be identical or different, represent methyl or phenyl; at least 60 mol % of all the radicals $R_{27}$ and $R'_{27}$ representing methyl;

$R_{28}$ represents $C_8$-$C_{20}$ alkyl or alkenyl;

R" represents a $C_2$-$C_{18}$ linear or branched divalent hydrocarbon-based alkylene radical;

r' is an integer ranging from 1 to 120;

p' is an integer ranging from 1 to 30;

q' is equal to 0 or is less than 0.5 p', p'+q' being an integer ranging from 1 to 30; the polyorganosiloxanes of formula (XII) may contain groups:

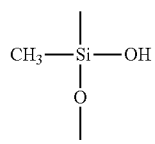

in units not exceeding 15% of the sum p'+q'+r';

anionic groups of carboxylic type, such as, for example, in the products described in patent EP 186 507 from the company Chisso Corporation, or of alkylcarboxylic type, such as those present in the product X-22-3701 E from the company Shin-Etsu; 2-hydroxyalkyl sulphonate; 2-hydroxyalkyl thiosulphate such as the products sold by the company Goldschmidt under the names ABIL S201 and ABIL S255;

hydroxyacylamino groups, such as the polyorganosiloxanes described in patent application EP 342 834. Mention may be made, for example, of the product Q2-8413 from the company Dow Corning.

According to at least one embodiment, it is also possible to use silicones comprising a polysiloxane portion and a portion comprising a non-silicone organic chain, one of the two portions constituting the main chain of the polymer, the other being grafted onto said main chain. These polymers are described, for example, in patent applications EP-A-412 704, EP-A-412 707, EP-A-640 105, WO 95/00578, EP-A-582 152 and WO 93/23009 and U.S. Pat. Nos. 4,693,935, 4,728,571 and 4,972,037. Those polymers can be anionic or non-ionic.

Such polymers are, for example, copolymers that can be obtained by free-radical polymerization starting with a monomer mixture comprising:

a) 50 to 90% by weight of tert-butyl acrylate;
b) 0 to 40% by weight of acrylic acid; and
c) 5 to 40% by weight of silicone macromer of formula:

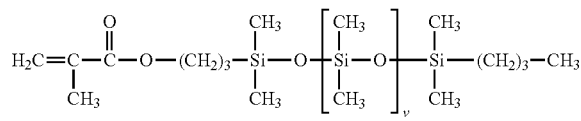

(XIII)

with v being a number ranging from 5 to 700; the weight percentages being relative to the total weight of the monomers.

Other examples of grafted silicone polymers are, for example, polydimethylsiloxanes (PDMS) onto which are grafted, via a connecting chain unit of thiopropylene type, mixed polymer units of poly(meth)acrylic acid type and of polyalkyl (meth)acrylate type, and polydimethylsiloxanes (PDMS) onto which are grafted, via a connecting chain unit of thiopropylene type, polymer units of polyisobutyl(meth)acrylate type.

According to at least one embodiment, the silicones can be in the form of emulsions, nanoemulsions or microemulsions.

According to at least one embodiment, the polyorganosiloxanes can be:

non-volatile silicones chosen from the family of polyalkylsiloxanes comprising trimethylsilyl end groups, such as oils having a viscosity ranging from 0.2 to 2.5 m$^2$/s at 25° C., such as the oils of the DC200 series from Dow Corning, further such as those with a viscosity of 60,000 cSt, of the Silbione 70047 and 47 series and even further such as the oil 70 047 V 500 000, which are sold by the company Rhodia Chimie, polyalkylsiloxanes comprising dimethylsilanol end groups, such as dimethiconols, or polyalkylarylsiloxanes such as the oil SILBIONE 70641 V 200 sold by the company Rhodia Chimie;

the organopolysiloxane resin, such as the products sold under the name DOW CORNING 593;

polysiloxanes comprising amine groups, such as amodimethicones or trimethylsilylamodimethicones.

Ceramides

According to at least one embodiment, the compounds of ceramide type are, for example, natural or synthetic ceramides and/or glycoceramides and/or pseudoceramides and/or neoceramides.

Compounds of ceramide type are described, for example, in patent applications DE 4 424 530, DE 4 424 533, DE 4 402 929, DE 4 420 736, WO 95/23807, WO 94/07844, EP-A-0 646 572, WO 95/16665, FR-2 673 179, EP-A-0 227 994, WO 94/07844, WO 94/24097 and WO 94/10131.

According to at least one embodiment, compounds of ceramide type can include, for example:

2-N-linoleoylaminooctadecane-1,3-diol,
2-N-oleoylaminooctadecane-1,3-diol,
2-N-palmitoylaminooctadecane-1,3-diol,
2-N-stearoylaminooctadecane-1,3-diol,
2-N-behenoylaminooctadecane-1,3-diol,
2-N-[2-hydroxypalmitoyl]aminooctadecane-1,3-diol,
2-N-stearoylaminooctadecane-1,3,4-triol and such as N-stearoylphytosphingosine,
2-N-palmitoylaminohexadecane-1,3-diol,
bis(N-hydroxyethyl-N-cetyl)malonamide,
N-(2-hydroxyethyl)-N-(3-cetyloxy-2-hydroxypropyl)cetylamide,
N-docosanoyl-N-methyl-D-glucamine,
or mixtures of these compounds.

Cationic Surfactants

It is also possible to use at least one cationic surfactant, among which mention may be made, for example, of: optionally polyoxyalkylenated primary, secondary or tertiary fatty amine salts; quaternary ammonium salts; imidazoline derivatives; or amine oxides of cationic nature.

Examples of quaternary ammonium salts include:
those of general formula (XIV) below:

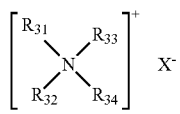

in which the radicals $R_{31}$ to $R_{34}$, which may be identical or different, represent a linear or branched aliphatic radical comprising from 1 to 30 carbon atoms, or an aromatic radical such as aryl or alkylaryl. The aliphatic radicals can comprise at least one heteroatom such as, oxygen, nitrogen, sulphur or halogen. The aliphatic radicals are chosen, for example, from alkyl, alkoxy, polyoxy($C_2$-$C_6$)alkylene, alkylamide, ($C_{12}$-$C_{22}$)alkylamido($C_2$-$C_6$)alkyl, ($C_{12}$-$C_{22}$)alkylacetate and hydroxyalkyl radicals, comprising from about 1 to 30 carbon atoms; X is an anion chosen from halides, phosphates, acetates, lactates, ($C_2$-$C_6$)alkyl sulphates, alkyl and alkylaryl sulphonates;

quaternary ammonium salts of imidazolinium, such as, for example, the salt of formula (XV) below:

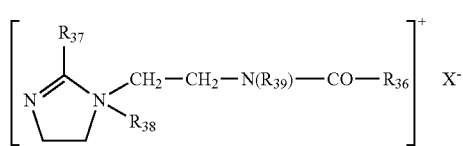

in which $R_{36}$ represents an alkenyl or alkyl radical comprising from 8 to 30 carbon atoms, for example tallow fatty acid derivatives, $R_{37}$ represents a hydrogen atom, a $C_1$-$C_4$ alkyl radical or an alkenyl or alkyl radical comprising from 8 to 30 carbon atoms, $R_{38}$ represents a $C_1$-$C_4$ alkyl radical, $R_{39}$ represents a hydrogen atom or a $C_1$-$C_4$ alkyl radical, X is an anion chosen from halides, phosphates, acetates, lactates, alkyl sulphates, alkyl and alkylaryl sulphonates. $R_{36}$ and $R_{37}$, for example, represent a mixture of alkenyl and/or alkyl radicals comprising from 12 to 21 carbon atoms, for example tallow fatty acid derivatives, $R_{38}$, for example, represents methyl and $R_{39}$, for example, represent hydrogen. Such a product is sold, for example, under the name REWOQUAT W 75 by the company Degussa;

diquaternary ammonium salts of formula (XVI):

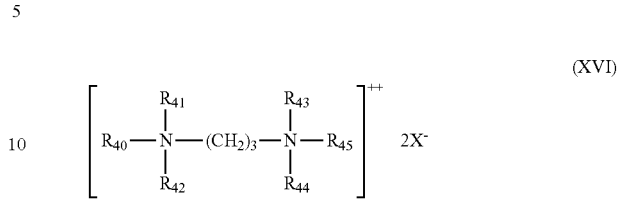

in which $R_{40}$ represents an aliphatic radical comprising from about 16 to 30 carbon atoms, $R_{41}$, $R_{42}$, $R_{43}$, $R_{44}$ and $R_{45}$, which may be identical or different, are chosen from hydrogen and an alkyl radical comprising from 1 to 4 carbon atoms, and X is an anion chosen from halides, acetates, phosphates, nitrates and methyl sulphates. Such diquaternary ammonium salts, for example, may comprise propane tallow diammonium dichloride;

quaternary ammonium salts comprising at least one ester function.

The quaternary ammonium salts comprising at least one ester function that may be used according to the disclosure are, for example, those of formula (XVII) below:

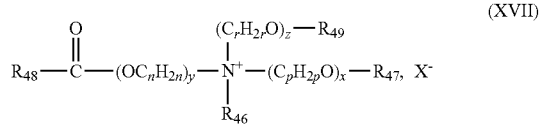

in which:

$R_{46}$ is chosen from $C_1$-$C_6$ alkyl radicals and $C_1$-$C_6$ hydroxyalkyl and dihydroxyalkyl radicals;

$R_{47}$ is chosen from:
a radical

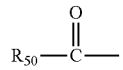

linear and branched, saturated and unsaturated $C_1$-$C_{22}$ hydrocarbon-based radicals $R_{51}$, and
a hydrogen atom, $R_{49}$ is chosen from:
a radical

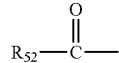

linear and branched, saturated and unsaturated $C_1$-$C_6$ hydrocarbon-based radicals $R_{53}$, and
a hydrogen atom, $R_{48}$, $R_{50}$ and $R_{52}$, which may be identical or different, are chosen from linear and branched, saturated and unsaturated $C_7$-$C_{21}$ hydrocarbon-based radicals;

n, p and r, which may be identical or different, are integers ranging from 2 to 6;

y is an integer ranging from 1 to 10;

x and z, which may be identical or different, are integers ranging from 0 to 10;

$X^-$ is a simple or complex, organic or inorganic anion;

with the proviso that the sum x+y+z is from 1 to 15, that when x is 0, then $R_{47}$ represents $R_{51}$ and that when z is 0, then $R_{49}$ represents $R_{53}$.

The $R_{46}$ alkyl radicals may be linear or branched and such as linear.

According to at least one embodiment, $R_{46}$ can represent a methyl, ethyl, hydroxyethyl or dihydroxypropyl radical and such as a methyl or ethyl radical.

The sum x+y+z is, for example, from 1 to 10.

When $R_{47}$ is a hydrocarbon-based radical $R_{51}$, it may be long and comprise from 12 to 22 carbon atoms, or short and comprise from 1 to 3 carbon atoms.

When $R_{49}$ is a hydrocarbon-based radical $R_{53}$, it, for example, may comprise 1 to 3 carbon atoms.

$R_{48}$, $R_{50}$ and $R_{52}$, which may be identical or different, are, for example, chosen from linear and branched, saturated and unsaturated $C_{11}$-$C_{21}$ hydrocarbon-based radicals, and such as from linear and branched, saturated and unsaturated, $C_{11}$-$C_{21}$ alkyl and alkenyl radicals.

x and z, which may be identical or different, are, for example, 0 or 1.

y can be, for example, equal to 1.

n, p and r, which may be identical or different, are, for example, 2 or 3 and further for example are equal to 2.

The anion $X^-$ is, for example, a halide (chloride, bromide or iodide) or an alkyl sulphate, such as methyl sulphate. However, methanesulphonate, phosphate, nitrate, tosylate, an anion derived from an organic acid, such as acetate or lactate, or any other anion that is compatible with the ammonium comprising an ester function, may be used.

The anion $X^-$ is, for example, chloride or methyl sulphate.

According to at least one embodiment, the ammonium salts can be those of formula (XVII) in which:

$R_{46}$ represents a methyl or ethyl radical, x and y are equal to 1;

z is equal to 0 or 1;

n, p and r are equal to 2;

$R_{47}$ is chosen from:

a radical

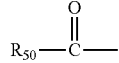

methyl, ethyl and $C_{14}$-$C_{22}$ hydrocarbon-based radicals; and a hydrogen atom;

$R_{49}$ is chosen from:

a radical

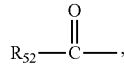

and a hydrogen atom;

$R_{48}$, $R_{50}$ and $R_{52}$, which may be identical or different, are chosen from linear and branched, saturated and unsaturated $C_{13}$-$C_{17}$ hydrocarbon-based radicals and such as from linear and branched, saturated and unsaturated $C_{13}$-$C_{17}$ alkyl and alkenyl radicals.

According to at least one embodiment, the hydrocarbon-based radicals are linear.

Examples of the compounds of formula (XVII) that may be mentioned include the diacyloxyethyldimethylammonium, diacyloxyethylhydroxyethylmethyl-ammonium, monoacyloxyethyldihydroxyethylmethylammonium, triacyl-oxyethylmethylammonium and monoacyloxyethylhydroxyethyldimethylammonium salts (chloride or methyl sulphate in particular), and mixtures thereof. The acyl radicals, for example, comprise 14 to 18 carbon atoms and can be obtained, for example, from a plant oil such as palm oil or sunflower oil. When the compound comprises several acyl radicals, these radicals may be identical or different.

These products can be obtained, for example, by direct esterification of triethanolamine, triisopropanolamine, an alkyldiethanolamine or an alkyldiisopropanolamine, which are optionally oxyalkylenated, with fatty acids or with fatty acid mixtures of plant or animal origin, or by transesterification of the methyl esters thereof. This esterification can be followed by a quaternization using an alkylating agent such as an alkyl halide (for example a methyl or ethyl halide), a dialkyl sulphate (for example dimethyl or diethyl sulphate), methyl methanesulphonate, methyl para-toluenesulphonate, glycol chlorohydrin or glycerol chlorohydrin.

Such compounds are sold, for example, under the names DEHYQUAT by the company Cognis, STEPANQUAT by the company Stepan, NOXAMIUM by the company CECA or REWOQUATWE 18 by the company Degussa.

It is also possible to use the ammonium salts comprising at least one ester function that are described, for example, in U.S. Pat. No. 4,874,554 and U.S. Pat. No. 4,137,180.

Among the quaternary ammonium salts of formula (XIV), mention may be made of, on the one hand, tetraalkylammonium chlorides such as, for example, dialkyldimethylammonium chlorides or alkyltrimethylammonium chlorides, in which the alkyl radical comprises from 12 to 22 carbon atoms, such as behenyltrimethylammonium chloride, distearyldimethylammonium chloride, cetyltrimethylammonium chloride, or benzyldimethylstearylammonium chloride, or, on the other hand, stearamido-propyldimethyl(myristyl acetate)ammonium chloride sold under the name CERAPHYL 70 by the company Van Dyk.

The saturated fatty acids that can be used for preparing quaternary ammonium salts of formula (XVII) can be chosen from myristic acid, palmitic acid, stearic acid, behenic acid and isostearic acid.

The fatty acid esters as disclosed herein for formula (XVII) other than plant oils are, for example, carboxylic acid esters, such as mono-, di-, tri- or tetracarboxylic esters.

The monocarboxylic acid esters can be linear or branched, saturated or unsaturated $C_1$-$C_{26}$ aliphatic acid monoesters of linear or branched, saturated or unsaturated, $C_1$-$C_{26}$ aliphatic alcohols, the total carbon number of the esters being greater than or equal to 10.

Among the monocarboxylic acid esters, mention may be made of dihydroabietyl behenate; octyldodecyl behenate; isocetyl behenate; cetyl lactate; $C_{12}$-$C_{15}$ alkyl lactate; isostearyl lactate; lauryl lactate; linoleyl lactate; oleyl lactate; (iso)stearyl octanoate; isocetyl octanoate; octyl octanoate; cetyl octanoate; decyl oleate; isocetyl isostearate; isocetyl laurate; isocetyl stearate; isodecyl octanoate; isodecyl oleate; isononyl isononanoate; isostearyl palmitate; methylacetyl ricinoleate; myristyl stearate; octyl isononanoate; 2-ethylhexyl isononate; octyl palmitate; octyl pelargonate; octyl stearate; octyldodecyl erucate; oleyl erucate; ethyl and isopropyl palmitates, 2-ethylhexyl palmitate, 2-octyldecyl palmitate, alkyl myristates such as isopropyl, butyl, cetyl or 2-octyldodecyl myristate, hexyl stearate, butyl stearate, isobutyl stearate; dioctyl malate, hexyl laurate, 2-hexyldecyl laurate, isostearyl neopentanoate, isodecyl neopentanoate.

$C_4$-$C_{22}$ di- or tricarboxylic acid esters of $C_1$-$C_{22}$ alcohols, and mono-, di- or tricarboxylic acid esters of $C_2$-$C_{26}$ di-, tri-, tetra- or pentahydroxy alcohols can also be used.

Mention may be made, for example, of: diethyl sebacate; diisopropyl sebacate; diisopropyl adipate; di-n-propyl adipate; dioctyl adipate; diisostearyl adipate; dioctyl maleate; glyceryl undecylenate; octyldodecylstearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate dicaprate; tridecyl erucate; triisopropyl citrate; triisostearyl citrate; glyceryl trilactate; glyceryl trioctanoate; trioctyldodecyl citrate; trioleyl citrate.

Among the esters mentioned above, further mention can be made of ethyl and isopropyl palmitates, 2-ethylhexyl palmitate, 2-octyldecyl palmitate, alkyl myristates such as isopropyl, butyl, cetyl or 2-octyldodecyl myristate, hexyl stearate, butyl stearate, isobutyl stearate; dioctyl malate, hexyl laurate, 2-hexyldecyl laurate, isononyl isononanoate, cetyl octanoate, isostearyl neopentanoate, isodecyl neopentanoate.

Fluoro Oils

The fluoro oils that can be used in the present disclosure include, for example, the perfluoropolyethers described in patent application EP-A-486 135, and the fluorohydrocarbon compounds such as described in patent application WO 93/11103.

The term "fluorohydrocarbon compounds" means compounds whose chemical structure comprises a carbon skeleton in which certain hydrogen atoms have been replaced with fluorine atoms.

The fluoro oils can also be fluorocarbons such as fluoroamines, for example perfluorotributylamine, fluorohydrocarbons, for example perfluorodecahydronaphthalene, fluoro esters and fluoro ethers.

The perfluoropolyethers are sold, for example, under the trade names FOMBLIN by the company Montefluos and KRYTOX by the company Du Pont.

Among the fluorohydrocarbon compounds, mention may also be made of fluorine-containing fatty acid esters such as the product sold under the name NOFABLE FO by the company Nippon Oil.

Needless to say, it is possible to use mixtures of conditioning agents.

According to at least one embodiment, the conditioning agents can be cationic polymers, cationic surfactants and silicones, and mixtures thereof.

According to at least one embodiment, the at least one conditioning agent may be present in a total amount ranging from 0.001% to 20% by weight, such as from 0.01% to 10% by weight, and further such as from 0.1% to 3% by weight, relative to the total weight of the final composition.

The compositions for protecting the color of artificially dyed keratin fibers according to the disclosure may be in the form of aqueous or aqueous-alcoholic lotions. The compositions according to the disclosure may also be in the form of an oil, a gel, a milk, a cream, an emulsion or a mousse.

These compositions may also be anhydrous, in other words may comprise less than 5% water.

The compositions for protecting the color of artificially dyed keratin fibers may be packaged in various forms, and such as in vaporizers, pump-dispenser bottles, or in aerosol containers in order to apply the composition in vaporized form or in the form of a mousse. Such packaging forms are indicated, for example, when it is desired to obtain a spray, a lacquer or a mousse for treating the hair.

The pH of the composition for protecting the color of artificially dyed keratin fibers may, for example, range from 1 to 11. It is for example from 2 to 6 for non-dyeing products, and can be adjusted to the desired value via acidifying or basifying agents that are known in the art for compositions applied to keratin fibers.

Among the basifying agents, mention may be made, by way of example, of aqueous ammonia, alkali metal carbonates, alkanolamines such as monoethanolamine, diethanolamine and triethanolamine and also derivatives thereof, oxyethylenated and/or oxypropylenated hydroxyalkylamines and ethylenediamines, sodium hydroxide, potassium hydroxide and compounds having the formula below:

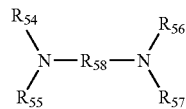

in which $R_{58}$ is a propylene residue optionally substituted with a hydroxyl group or a $C_1$-$C_4$ alkyl radical; $R_{54}$, $R_{55}$, $R_{58}$ and $R_{57}$, which may be identical or different, represent a hydrogen atom, a $C_1$-$C_4$ alkyl radical or a $C_1$-$C_4$ hydroxyalkyl radical.

The acidifying agents are, by way of example, mineral or organic acids, for instance hydrochloric acid or orthophosphoric acid, carboxylic acids, for instance tartaric acid, citric acid or lactic acid, or sulphonic acids.

Also provided is a method for wash-protecting the color of artificially dyed keratin fibers, comprising applying to said fibers, before or after dyeing, at least one drying oil or at least one composition comprising, in a cosmetically acceptable medium, at least one drying oil.

For example, the composition comprising the at least one drying oil can be applied to said fibers after the dyeing step.

The method may also comprise a step of rinsing and/or a step of washing with shampoo before or after the application of the composition comprising the at least one drying oil.

The method according to the disclosure may further comprise an additional step of total or partial drying of the keratin fibers.

According to at least one embodiment, the method for protecting the color of keratin fibers may comprise a step of heating the composition comprising the at least one drying oil, which will then be applied directly to the keratin fibers. The temperature can be, for example, less than or equal to 120° C.

According to at least one embodiment, the method for protecting the color of keratin fibers may also comprise a step of heating the keratin fibers during or after application of the composition comprising at least one drying oil.

The heating of the keratin fibers may be performed, for example, via an iron, a liquid water/steam mixture or with a heating hood.

The heating iron that is useful in the context of the disclosure is a heating iron that can be used in the field of hair care. Such an iron, for example a crimping iron or a smoothing iron, may be well known in the field of hair treatment. For example, irons as disclosed herein can be flat or round irons described, for example, in U.S. Pat. No. 4,103,145, U.S. Pat. No. 4,308,878, U.S. Pat. No. 5,983,903, U.S. Pat. No. 5,957, 140 and U.S. Pat. No. 5,494,058. The iron may be applied by successive separate touches of a few seconds, or by gradually moving it or sliding it along the locks. It is possible, between the application of the color-protecting composition and the application of the heating iron to the keratin fibers, to envisage a pause time. Said pause time can, for example, range from 30 seconds to 60 minutes, and such as from 1 to 30 minutes. The temperature may, for example, range from 60° C. to 120° C.

The liquid water/steam mixture that can be used in the context of the disclosure may, for example, have a temperature of at least 35° C.

The liquid water/steam mixture may constitute a mist. Said mixture can also comprise at least one other gas such as oxygen or nitrogen, mixtures of gases such as air, or other vaporizable compounds.

The temperature of the liquid water/steam mixture can, for example, be greater than or equal to 40° C., and such as ranging from 40° C. to 75° C.

According to at least one embodiment, the liquid water/steam mixture is brought into contact with the fiber for a period ranging from 1 second to 1 hour, and such as from 5 minutes to 15 minutes. Of course, the application of said mixture can be repeated several times on the same fiber, each operation being performed for a period as indicated above.

The liquid water/steam mixture used according to the disclosure can be produced using any apparatus known per se and intended for this purpose. However, according to the disclosure, an apparatus comprising at least one steam generator directly connected to a hood that diffuses the liquid water/steam mixture onto the keratin fibers, for example, human hair, can be used. This type of apparatus can be that, for example, sold under the name MICROMIST® by the company Takara Belmont.

Provided herein is a method for dyeing keratin fibers comprising
applying to the keratin fibers, at least one dye composition, for a time sufficient to develop the color, and
applying to the keratin fibers a drying oil composition comprising, in a cosmetically acceptable medium, at least one drying oil.

The application of the at least one dye composition may be followed by rinsing and/or drying of the keratin fibers.

The application of the drying oil composition may be followed by rinsing and/or drying of the keratin fibers. The drying oil composition may be preheated under the same conditions defined above. The application of the drying oil composition may be followed by heating of the keratin fibers under the same conditions defined above.

According to at least one embodiment, the drying oil composition can be applied after the application of the at least one dye composition. The drying oil composition may be applied immediately after dyeing, or after a delay. The term "after a delay" means an application that takes place a few hours or one or several days (from 1 to 15 days) after dyeing. According to at least one embodiment, the drying oil composition can be applied immediately after dyeing the keratin fibers; it being possible for the application of the drying oil composition to be repeated between two dyeing operations.

In the case of lightening direct dyeing operations, the at least one dye composition can be obtained from mixing, at the time of use, at least one composition comprising at least one direct dye optionally with at least one composition comprising at least one oxidizing agent.

In the case of oxidation dyeing operations, the at least one dye composition can be obtained by mixing, at the time of use, at least one composition comprising at least one oxidation base optionally with at least one coupler and/or at least one direct dye with at least one composition comprising at least one oxidizing agent.

Also provided is a method for dyeing keratin fibers comprising applying, to the keratin fibers, at least one dye composition comprising at least one direct dye and/or at least one oxidation base for a time sufficient to develop the color, wherein said at least one dye composition further comprises, in a cosmetically acceptable medium, at least one drying oil.

The at least one direct dye can be, for example, compounds that absorb light radiation in the visible range (400-750 nm). They may be non-ionic, anionic or cationic in nature.

For example, the at least one direct dye can be chosen from nitrobenzene dyes and azo, anthraquinone, naphthoquinone, benzoquinone, phenothiazine, indigoid, xanthene, phenanthridine, phthalocyanin and triarylmethane-derived dyes.

Among the nitrobenzene dyes that may be mentioned are, for example, the following red or orange compounds: 1-hydroxy-3-nitro-4-N-(γ-hydroxypropyl)aminobenzene, N-(β-hydroxyethyl)amino-3-nitro-4-aminobenzene, 1-amino-3-methyl-4-N-(β-hydroxyethyl)amino-6-nitrobenzene, 1-hydroxy-3-nitro-4-N-(β-hydroxyethyl)amino-benzene, 1,4-diamino-2-nitrobenzene, 1-amino-2-nitro-4-methylaminobenzene, N-(β-hydroxyethyl)-2-nitro-para-phenylenediamine, 1-amino-2-nitro-4-(β-hydroxyethyl)-amino-5-chlorobenzene, 2-nitro-4-aminodiphenylamine, 1-amino-3-nitro-6-hydroxybenzene, 1-(β-aminoethyl)amino-2-nitro-4-(3-hydroxyethyloxy)benzene, 1-(β,γ-dihydroxypropyl)oxy-3-nitro-4-(β-hydroxyethyl)aminobenzene, 1-hydroxy-3-nitro-4-aminobenzene, 1-hydroxy-2-amino-4,6-dinitrobenzene, 1-methoxy-3-nitro-4-(3-hydroxyethyl)aminobenzene, 2-nitro-4'-hydroxydiphenylamine, 1-amino-2-nitro-4-hydroxy-5-methylbenzene, alone or as mixtures.

As regards the nitrobenzene direct dyes, mention may be made of dyes of yellow and green-yellow type, for instance 1-β-hydroxyethyloxy-3-methylamino-4-nitro-benzene, 1-methylamino-2-nitro-5-(β,γ-dihydroxypropyl)oxybenzene, 1-(β-hydroxyethyl)amino-2-methoxy-4-nitrobenzene, 1-(β-aminoethyl)amino-2-nitro-5-methoxybenzene, 1,3-bis(β-hydroxyethyl)amino-4-nitro-6-chlorobenzene, 1-amino-2-nitro-6-methylbenzene, 1-(β-hydroxyethyl)amino-2-hydroxy-4-nitrobenzene, N-(β-hydroxyethyl)-2-nitro-4-trifluoromethylaniline, 4-(β-hydroxyethyl)amino-3-nitrobenzenesulphonic acid, 4-ethylamino-3-nitrobenzoic acid, 4-(β-hydroxyethyl)amino-3-nitrochlorobenzene, 4-(β-hydroxyethyl)amino-3-nitromethylbenzene, 4-(β,γ-dihydroxypropyl)amino-3-nitrotrifluoromethylbenzene, 1-(β-ureidoethyl)amino-4-nitrobenzene, 1,3-diamino-4-nitrobenzene, 1-hydroxy-2-amino-5-nitrobenzene, 1-amino-2-[tris(hydroxymethyl)methyl]amino-5-nitrobenzene, 1-(β-hydroxyethyl)amino-2-nitrobenzene and 4-(β-hydroxyethyl)amino-3-nitrobenzamide.

Mention may also be made of blue or violet nitrobenzene dyes, for instance, inter alia, 1-(β-hydroxyethyl)amino-4-N,N-bis(β-hydroxyethyl)amino-2-nitrobenzene, 1-(γ-hydroxypropyl)amino-4-N,N-bis(β-hydroxyethyl)amino-2-nitrobenzene, 1-(β-hydroxy-ethyl)amino-4-(N-methyl, N-β-hydroxyethyl)amino-2-nitrobenzene, 1-(β-hydroxyethyl)amino-4-(N-ethyl, N-β-hydroxyethyl)amino-2-nitrobenzene, 1-(β,γ-dihydroxypropyl)amino-4-(N-ethyl, N-β-hydroxyethyl)amino-2-nitrobenzene, the 2-nitro-para-phenylenediamines of the following formula:

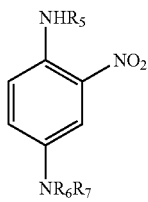

in which:
R$_6$ represents a C$_1$-C$_4$ alkyl radical or a β-hydroxyethyl, β-hydroxypropyl or γ-hydroxypropyl radical;
R$_5$ and R$_7$, which may be identical or different, represent a β-hydroxyethyl, β-hydroxypropyl, γ-hydroxypropyl or β,γ-dihydroxypropyl radical, at least one of the radicals R$_6$, R$_7$ or R$_5$ representing a γ-hydroxypropyl radical and R$_6$ and R$_7$ not being able to simultaneously represent a β-hydroxyethyl radical when R$_6$ is a γ-hydroxypropyl radical, such as those described in French patent FR 2 692 572.

It is recalled that azo dyes can be compounds comprising in their structure at least one —N=N— sequence not included in a ring; methine dyes can be compounds comprising in their structure at least one —C=C— sequence not included in a ring; azomethine dyes are compounds comprising in their structure at least one —C=N— sequence not included in a ring.

The triarylmethane-based dyes may comprise in their structure at least one sequence below:

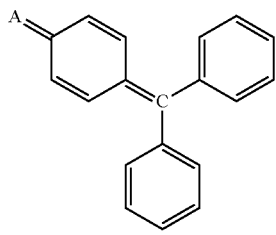

Wherein A represents an oxygen or nitrogen atom.

The xanthene dyes may comprise in their structure at least one sequence of formula:

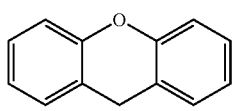

The phenanthridine dyes may comprise in their structure at least one sequence of formula:

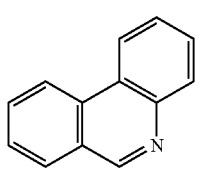

The phthalocyanin dyes may comprise in their structure at least one sequence of formula:

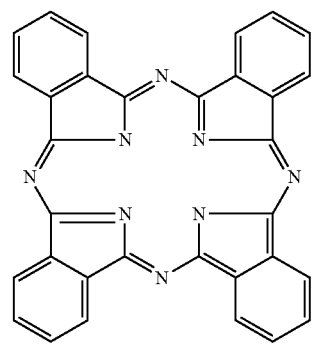

The phenothiazine dyes may comprise in their structure at least one sequence below:

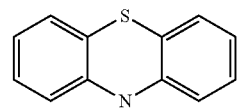

The direct dyes may moreover be chosen from basic dyes like those listed in the Color Index, 3rd edition, for example under the names BASIC BROWN 16, BASIC BROWN 17, BASIC YELLOW 57, BASIC RED 76, BASIC VIOLET 10, BASIC BLUE 26 and BASIC BLUE 99; or from the acidic direct dyes listed in the Color Index, 3rd edition, under the names ACID ORANGE 7, ACID ORANGE 24, ACID YELLOW 36, ACID RED 33, ACID RED 184, ACID BLACK 2, ACID VIOLET 43, and ACID BLUE 62, or cationic direct dyes such as those described in patent applications WO 95/01772, WO 95/15144 and EP 714 954 and such as BASIC RED 51, BASIC ORANGE 31 and BASIC YELLOW 87.

The at least one direct dye can be present in a total amount ranging from 0.0005% to 12% by weight, relative to the total weight of the dye composition and such as from 0.005% to 6% by weight relative to the total weight of the dye composition.

The oxidation bases may be chosen from the oxidation bases conventionally used in oxidation dyeing, among which mention may, for example, be made of para-phenylenediamines, bis(phenyl)alkylenediamines, para-aminophenols, ortho-aminophenols and heterocyclic bases.

Among the para-phenylenediamines that may be mentioned, for example, are para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, N,N-diethyl-4-amino-3-methylaniline, N,N-bis(β-hydroxyethyl)-para-phenylenediamine, 4-N,N-bis(β-hydroxyethyl)amino-2-methylaniline, 4-N,N-bis(β-hydroxy-ethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine and N-(β-methoxyethyl)-para-phenylenediamine, and the acid addition salts thereof.

Exemplary mention of para-phenylenediamines can further be made of: para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the acid addition salts thereof.

Among the bis(phenyl)alkylenediamines that may be mentioned, for example, are N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-amino-phenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,5-dioxaoctane, and the acid addition salts thereof.

Among the para-aminophenols that may be mentioned, for example, are para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxy-ethylaminomethyl)phenol and 4-amino-2-fluorophenol, and the acid addition salts thereof.

Among the ortho-aminophenols that may be mentioned, for example, are 2-aminophenol, 2-amino-5-methylphenol, 2-amino-6-methylphenol and 5-acetamido-2-aminophenol, and the acid addition salts thereof.

Among the heterocyclic bases that may be mentioned, for example, are pyridine derivatives, pyrimidine derivatives and pyrazole derivatives.

Among the pyridine derivatives that may be mentioned, for example, are the compounds described, for example, in patents GB 1 026 978 and GB 1 153 196, such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine and 3,4-diamino-pyridine, and the acid addition salts thereof.

Among the pyrimidine derivatives that may be mentioned include, for example, the compounds described, for example, in patents DE 2 359 399; JP 88-169 571; JP 05-163 124; EP 0 770 375 or patent application WO 96/15765, such as 2,4,5,6-tetraminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, and pyrazolopyrimidine derivatives such as those mentioned in patent application FR-A-2 750 048 and among which exemplary mention may be made of pyrazolo[1,5-a]-pyrimidine-3,7-diamine; 2,5-dimethylpyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-amino-pyrazolo[1,5-a]pyrimidin-7-ol; 3-aminopyrazolo[1,5-a]pyrimidin-5-ol; 2-(3-amino-pyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)(2-hydroxyethyl)amino]ethanol, 2-[(7-aminopyrazolo[1,5-a]pyrimidin-3-yl)(2-hydroxyethyl)amino]ethanol, 5,6-dimethylpyrazolo[1,5-a]pyrimidine-3,7-diamine, 2,6-dimethylpyrazolo[1,5-a]pyrimidine-3,7-diamine, 2,5,N7,N7-tetramethylpyrazolo[1,5-a]pyrimidine-3,7-diamine and 3-amino-5-methyl-7-imidazolylpropylaminopyrazolo[1,5-a]pyrimidine, and the acid addition salts thereof and the tautomeric forms thereof, when a tautomeric equilibrium exists.

Among the pyrazole derivatives that may be mentioned, for example, are the compounds described, for example, in patents DE 3 843 892 and DE 4 133 957 and patent applications WO 94/08969, WO 94/08970, FR-A-2 733 749 and DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenyl-pyrazole, 4-amino-1,3-dimethyl-5-hydrazinopyrazole, 1-benzyl-4,5-diamino-3-methyl-pyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-tri-aminopyrazole, 3,5-diamino-1-methyl-4-methylaminopyrazole and 3,5-diamino-4-(β-hydroxyethyl)amino-1-methylpyrazole, and the acid addition salts thereof.

By way of pyrazole derivatives, mention may also be made of diamino-N,N-dihydropyrazolopyrazolones, and for example those described in application FR 2 886 136, such as the following compounds and the acid addition salts thereof:

2,3-diamino-6,7-dihydro-1H,5H-pyrazolo[1,2-a]pyrazol-1-one,
2-amino-3-ethylamino-6,7-dihydro-1H,5H-pyrazolo[1,2-a]pyrazol-1-one,
2-amino-3-isopropylamino-6,7-dihydro-1H,5H-pyrazolo[1,2-a]pyrazol-1-one,
2-amino-3-(pyrrolidin-1-yl)-6,7-dihydro-1H,5H-pyrazolo[1,2-a]pyrazol-1-one,
4,5-diamino-1,2-dimethyl-1,2-dihydropyrazol-3-one,
4,5-diamino-1,2-diethyl-1,2-dihydropyrazol-3-one,
4,5-diamino-1,2-di(2-hydroxyethyl)-1,2-dihydropyrazol-3-one,
2-amino-3-(2-hydroxyethyl)amino-6,7-dihydro-1H,5H-pyrazolo[1,2-a]pyrazol-1-one,
2-amino-3-dimethylamino-6,7-dihydro-1H,5H-pyrazolo[1,2-a]pyrazol-1-one,
2,3-diamino-5,6,7,8-tetrahydro-1H,6H-pyridazino[1,2-a]pyrazol-1-one,
4-amino-1,2-diethyl-5-(pyrrolidin-1-yl)-1,2-dihydropyrazol-3-one,
4-amino-5-(3-dimethylaminopyrrolidin-1-yl)-1,2-diethyl-1,2-dihydropyrazol-3-one, and
2,3-diamino-6-hydroxy-6,7-dihydro-1H,5H-pyrazolo[1,2-a]pyrazol-1-one.

As heterocyclic bases or acid addition salts thereof, further exemplary mention may be made of 4,5-diamino-1-(β-hydroxyethyl)pyrazole and/or 2,3-diamino-6,7-dihydro-1H,5H-pyrazolo[1,2-a]pyrazol-1-one and acid addition salts thereof.

The at least one oxidation base can be present in a total amount ranging from 0.0005% to 12% by weight, relative to the total weight of the dye composition, and such as from 0.005% to 6% by weight, relative to the total weight of the dye composition.

The oxidation dye compositions in accordance with the disclosure may also comprise at least one coupler and/or at least one direct dye, for example, to modify the shades or to enrich them with tints.

The at least one coupler that can be used in the oxidation dye compositions according to the disclosure may be chosen from the couplers that can be used in oxidation dyeing, and among which mention may be made, for example, of meta-phenylenediamines, meta-aminophenols, meta-diphenols, naphthols and heterocyclic couplers, for instance indole derivatives, indoline derivatives, pyridine derivatives, indazole derivatives, pyrazolo[1,5-b]-1,2,4-triazole derivatives, pyrazolo[3,2-c]-1,2,4-triazole derivatives, benzimidazole derivatives, benzothiazole derivatives, benzoxazole derivatives, 1,3-benzodioxole derivatives and pyrazolones, and the acid addition salts thereof.

The at least one coupler can also be chosen from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, sesamol, α-naphthol, 2-methyl-1-naphthol, 6-hydroxyindole, 4-hydroxyindole, 4-hydroxy-N-methylindole, 6-hydroxyindoline, 6-hydroxybenzomorpholine, 3,5-diamino-2,6-dimethoxypyridine, 1-N(β-hydroxyethyl)amino-3,4-methylenedioxybenzene, 2,6-bis(β-hydroxyethylamino) toluene, 2,6-dihydroxy-4-methylpyridine, 1H-3-methylpyrazol-5-one, 1-phenyl-3-methylpyrazol-5-one, and the acid addition salts thereof.

The at least one coupler may be present in a total amount ranging from 0.0001% to 10% by weight, relative to the total weight of the dye composition, and such as from 0.005% to 5% by weight, relative to the total weight of the dye composition.

The dye composition in accordance with the disclosure may also comprise at least one adjuvant that can be used in hair dye compositions, such as anionic, cationic, non-ionic, amphoteric or zwitterionic surfactants or mixtures thereof, anionic, cationic, non-ionic, amphoteric or zwitterionic polymers or blends thereof, mineral or organic thickeners, antioxidants, penetration agents, sequestering agents, fragrances, buffers, dispersants, conditioning agents, for instance silicones, film-forming agents, preservatives and opacifiers.

Of course, those skilled in the art will take care to select the at least one optional additional compound in such a way that the beneficial properties intrinsically associated with the dye composition in accordance with the disclosure are not, or are not substantially, adversely affected by the envisaged addition(s).

The dye composition according to the disclosure may be in various forms, such as in the form of liquids, creams or gels, or in any other form that is suitable for dyeing keratin fibers, and such as human hair.

The at least one oxidizing agent, used in lightening direct dyeing (direct dyeing with an oxidizing agent) or in oxidation dyeing, can be, for example, chosen from hydrogen peroxide, urea peroxide, alkali metal bromates or ferricyanides, and persalts such as perborates and persulphates. It is also possible to use, as oxidizing agent, at least one redox enzyme such as laccases, peroxidases and 2-electron oxidoreductases (such as uricase), where appropriate in the presence of the respective donor or cofactor thereof. According to at least one embodiment, hydrogen peroxide is used as the at least one oxidizing agent.

Also provided is a multi-compartment kit comprising
at least one first compartment comprising at least one composition comprising, in a cosmetically acceptable medium, at least one drying oil,
at least one second compartment comprising at least one dye composition comprising at least one oxidation base and/or at least one direct dye, and
optionally at least one third compartment comprising at least one oxidizing agent.

A multi-compartment kit comprising
at least one first compartment comprising at least one dye composition comprising, in a cosmetically acceptable medium, at least one drying oil, and at least one oxidation base and/or at least one direct dye, and
at least one second compartment comprising at least one oxidizing agent The following examples are intended to illustrate the disclosure without limiting the scope thereof.

Unless otherwise mentioned, the concentrations are relative to active materials.

EXAMPLE 1

Oil

The following composition comprising at least one drying oil to be applied before a shampoo, was prepared:
Partially Polymerized Linseed Oil

| | |
|---|---|
| (STANDOLIE DE LIN [linseed stand oil] 60 P from Novance) | 30 g |
| Salicylic acid | 0.1 g |
| Preservative | 0.1 g |
| Liquid petroleum jelly qs | 100 g |

EXAMPLE 2

Shampoo

The following shampoos were prepared:

| | A<br>In accordance with the disclosure | B<br>comparative |
|---|---|---|
| Sodium chloride | 2.3 g | 2.3 g |
| Partially polymerized linseed oil (STANDOLIE DE LIN [linseed stand oil] 60 P from Novance) | 1 g | — |
| Salicylic acid | 0.2 g | 0.2 g |
| Preservatives | qs | qs |
| Poly(dimethyldiallylammonium chloride) in water at 40% (MERQUAT 100 from Nalco) | 0.4 g | 0.4 g |
| Sodium lauryl ether sulphate (comprising 2.2 mol of ethylene oxide) in an aqueous solution at 70% AM | 4.9 g | 4.9 g |
| Cocoyl amidopropyl betaine in an aqueous solution at 30% of AM | 6.9 g | 6.9 g |
| Polyethoxylated (55 eo) propylene glycol and propylene glycol oleate in aqueous-glycolic solution (ANTIL 141 LIQUID from Evonik Goldschmidt) | 0.48 g | 0.48 g |
| Hexylene glycol | 1 g | 1 g |
| pH agent (NaOH or citric acid) qs pH | 5.3 | 5.3 |
| Deionized water qs | 100 g | 100 g |

Demonstration of the color-protecting effect with respect to washing

Dyeing Step:

A weight-for-weight mixture of the composition of Table 1 below and of aqueous hydrogen peroxide solution (L'Oeéal Professional 20-volumes 6% aqueous hydrogen peroxide solution) was applied to permanent-waved locks of hair comprising 90% white hairs in sufficient amount for the locks to be well impregnated (in this case, 10 g of dye mixture/g of lock). The leave-in time was 15 minutes on each side of the lock. The locks were then rinsed with water and then washed with DOP Camomile shampoo and dried.

TABLE 1

| Dye composition 1 | % amounts |
|---|---|
| Polyglycerolated oleyl alcohol comprising 2 mol of glycerol | 4 g |
| Polyglycerolated oleyl alcohol comprising 4 mol of glycerol (78% AM) | 5.69 g |
| Oleic acid | 3 g |
| Oleic amine 2 EO sold under the name ETHOMEEN 012 by the company Akzo | 7 g |
| Diethylaminopropyl laurylamino succinamate, sodium salt containing 55% AM | 3 g |
| Oleyl alcohol | 5 g |
| Oleic acid diethanolamide | 12 g |
| Propylene glycol | 3.5 g |
| Ethyl alcohol | 7 g |
| Dipropylene glycol | 0.5 g |
| Propylene glycol monomethyl ether | 9 g |
| Sodium metabisulphite in an aqueous solution containing 35% AM | 0.455 g |
| Ammonium acetate | 0.8 g |
| Antioxidant, sequestering agent | qs |
| Fragrance, preservative | qs |
| p-Phenylenediamine | $6 \times 10^{-4}$ mol |
| 4-Amino-2-hydroxytoluene | $6 \times 10^{-4}$ mol |
| Aqueous ammonia containing 20% of $NH_3$ | 10 g |
| Demineralized water | qs 100 g |

Protective Treatment Steps:

The following procedure was carried out:
Application of composition A or B of Example 2 in sufficient amount for the locks to be well impregnated (in this case, 2.5 grams per gram of hair on the dyed hair).
5 minutes leave-in time.
Rinsing and drying under a hood.

Steps of Color-Fastness after Shampoo Washing:

The above treated locks then underwent a shampoo wash-fastness test.

For this, the locks treated with composition A were shampooed 8 times successively with composition A, and the locks treated with composition B were shampooed 8 times successively with composition B, with intermediate drying.

Evaluation of the Protection

The degradation of the color after washing of the locks treated with composition A or B was evaluated visually relative to dyed locks that have not been washed.

These evaluations were accompanied by spectrocolorimetric monitoring.

Measurements were taken using a Minolta CM2022 spectrocolorimeter:

The degradation caused by the washing was expressed as $\Delta E$ $$\Delta E(\text{8 shampooing operations}-\text{0 shampooing operation}) = \sqrt{(\Delta L^{*2} + \Delta a^{*2} + \Delta b^{*2})}$$

The protection was then expressed through a difference in $\Delta E$ between the treated and untreated locks.

Results:

After the wash-fastness test, a substantial degradation of the color of the untreated dyed locks (i.e., those treated with composition B) was observed.

It was observed, surprisingly, that, after this same test, the use of the composition A in accordance with the disclosure afforded significant protection of the color relative to the untreated locks.

These results were confirmed by the colorimetric measurements, which indicated a significant gain in $\Delta E$ relative to the untreated lock after 8 shampooing operations.

Results of Color Protection after Wash-Fastness Test

| Lock | $\Delta E$ relative to the unwashed locks |
|---|---|
| Lock treated with the composition B after 8 shampooing operations | 9.83 |
| Lock treated with the composition A according to the disclosure after 8 shampooing operations | 5.72 |

The smaller the $\Delta E$, the smaller the amount of degradation of the color after washing. Composition A showed significantly better resistance to washing.

EXAMPLE 3

Shampoo

The following shampoo was prepared:
Partially Polymerized Linseed Oil

| | |
|---|---|
| (STANDOLIE DE LIN [linseed stand oil] 60P from Novance) | 0.1 g |
| Salicylic acid | 0.2 g |
| Preservatives | qs |
| Poly(dimethyldiallylammonium chloride) in water at 40% (MERQUAT 100 from Nalco) | 0.4 g |
| Sodium lauryl ether sulphate comprising 2.2 mol of ethylene oxide in an aqueous solution containing 70% AM | 4 g |
| Cocoylamidopropylbetaine in an aqueous solution containing 30% of AM | 4.4 g |
| (C8/C16) alkyl polyglucoside (1.4) in an aqueous solution containing 53% of AM | 5 g |
| Lauryl ether carboxylic acid (4.5 EO) (EMPICOL CED 5/FL from Huntsman) | 2.97 g |
| Propylene glycol | 2 g |
| Fragrance | 0.5 g |
| pH agent | qs pH 5.3 |
| Deionized water qs | 100 g |

This shampoo protected the color of artificially dyed hair.

EXAMPLE 4

Conditioner

The following conditioner was prepared:

| | |
|---|---|
| Cetylstearyl alcohol (C16/C18 50/50) | 2.5 g |
| Myristyl/cetyl/stearyl myristate/palmitate/stearate mixture (MIRACETI from Laserson) | 0.5 g |
| Palm oil | 2 g |
| Partially polymerized linseed oil (STANDOLIE DE LIN [linseed stand oil] 60P from Novance) | 1 g |

-continued

| | |
|---|---|
| Preservatives | 0.33 g |
| Oxyethylenated cetylstearyl alcohol (33 EO) | 0.8 g |
| Fragrance | 0.4 g |
| Pregelatinized hydroxypropyl corn distarch phosphate in an aqueous solution containing 90% AM (STRUCTURE ZEA from Akzo Nobel) | 4.5 g |
| pH agent | qs pH 5.3 |
| Deionized water qs | 100 g |

This conditioner protected the color of artificially dyed hair.

What is claimed is:

1. A method for wash-protecting the color of artificially dyed keratin fibers comprising
    applying to the artificially dyed keratin fibers at least one drying oil or at least one composition comprising, in a cosmetically acceptable medium, at least one drying oil, wherein the at least one drying oil is chosen from linseed oil, China wood oil, oiticica oil, vernonia oil, poppyseed oil, pomegranate oil, calendula oil and perilla oil.

2. The method according to claim 1, wherein the artificially dyed keratin fibers are the human hair.

3. The method according to claim 1, wherein the artificially dyed keratin fibers are dyed via oxidation dyeing, in the presence of at least one oxidizing agent.

4. The method according to claim 1, wherein the at least one drying oil is linseed oil.

5. The method according to claim 1, wherein the at least one drying oil is a refined oil.

6. The method according to claim 1, wherein the at least one drying oil is partially polymerized by heating or blowing.

7. The method according to claim 1, wherein the at least one drying oil is chosen from linseed stand oils.

8. The method according to claim 1, wherein the at least one drying oil is present in a total amount ranging from 0.05% to 100% by weight, relative to the total weight of the composition.

9. The method according to claim 8, wherein the at least one drying oil is present in a total amount ranging from 0.5% to 10% by weight, relative to the total weight of the composition.

10. A method for dyeing keratin fibers comprising
    applying to the keratin fibers, at least one dye composition, for a time sufficient to develop the color, and
    applying to the keratin fibers at least one drying oil composition comprising, in a cosmetically acceptable medium, at least one drying oil, wherein the at least one drying oil is chosen from linseed oil, China wood oil, oiticica oil, vernonia oil, poppyseed oil, pomegranate oil, calendula oil and perilla oil.

11. The method according to claim 10, further comprising rinsing and/or drying of the artificially dyed keratin fibres after applying the at least one dye composition.

12. The method according to claim 10, further comprising rinsing and/or drying and/or heating of the artificially dyed keratin fibres after applying the at least one drying oil composition.

13. The method according to claim 10, comprising applying the at least one drying oil composition after applying the at least one dye composition, wherein the application of said at least one drying oil composition is optionally repeated between two applications of the at least one dye composition.

14. The method according to claim 10, wherein the at least one dye composition is obtained by mixing, at the time of use, at least one composition comprising at least one direct dye optionally with at least one composition comprising at least one oxidizing agent.

15. The method according to claim 10, wherein the at least one dye composition is obtained by mixing, at the time of use, at least one composition comprising at least one oxidation base optionally with at least one coupler and/or at least one direct dye with at least one composition comprising at least one oxidizing agent.

16. A method for dyeing keratin fibers comprising applying, to the keratin fibers, at least one dye composition comprising at least one direct dye and/or at least one oxidation base for a time sufficient to develop the color, wherein said at least one dye composition further comprises, in a cosmetically acceptable medium, at least one drying oil chosen from linseed oil, China wood oil, oiticica oil, vernonia oil, poppyseed oil, pomegranate oil, calendula oil and perilla oil.

17. A multi-compartment kit comprising
    at least one first compartment comprising at least one composition comprising, in a cosmetically acceptable medium, at least one drying oil chosen from linseed oil, China wood oil, oiticica oil, vernonia oil, poppyseed oil, pomegranate oil, calendula oil and perilla oil,
    at least one second compartment comprising at least one dye composition comprising at least one oxidation base and/or at least one direct dye, and
    optionally at least one third compartment comprising at least one oxidizing agent.

18. A multi-compartment kit comprising
    at least one first compartment comprising at least one dye composition comprising, in a cosmetically acceptable medium, at least one drying oil, and at least one oxidation base and/or at least one direct dye, and
    at least one second compartment comprising at least one oxidizing agent, wherein the at least one drying oil is chosen from linseed oil, China wood oil, oiticica oil, vernonia oil, poppyseed oil, pomegranate oil, calendula oil and perilla oil.

* * * * *